(12) United States Patent
Pagel et al.

(10) Patent No.: US 11,628,229 B2
(45) Date of Patent: Apr. 18, 2023

(54) METHOD OF SYNTHESIZING $^{18}$F RADIOLABELED BIOMOLECULAR AGENTS

(71) Applicant: ARIZONA BOARD OF REGENTS ON BEHALF OF THE UNIVERSITY OF ARIZONA, Tucson, AZ (US)

(72) Inventors: Mark D. Pagel, Tucson, AZ (US); Iman Daryaei, Tucson, AZ (US); Abigail Shepard, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 82 days.

(21) Appl. No.: 16/493,668

(22) PCT Filed: Mar. 13, 2018

(86) PCT No.: PCT/US2018/022160
§ 371 (c)(1),
(2) Date: Sep. 12, 2019

(87) PCT Pub. No.: WO2018/169942
PCT Pub. Date: Sep. 20, 2018

(65) Prior Publication Data
US 2020/0009274 A1   Jan. 9, 2020

Related U.S. Application Data

(60) Provisional application No. 62/470,735, filed on Mar. 13, 2017.

(51) Int. Cl.
*A61K 51/04*   (2006.01)
(52) U.S. Cl.
CPC ................................. *A61K 51/0497* (2013.01)
(58) Field of Classification Search
CPC .................................................. A61K 51/0497
USPC ...................................................... 424/1.89
See application file for complete search history.

(56) References Cited

U.S. PATENT DOCUMENTS

| | | | |
|---|---|---|---|
| 2007/0092441 A1* | 4/2007 | Wadsworth | C07D 401/12 424/1.11 |
| 2012/0022227 A1 | 1/2012 | Olberg et al. | |
| 2013/0189185 A1 | 7/2013 | Li et al. | |

FOREIGN PATENT DOCUMENTS

WO    WO-2016030329 A1 *   3/2016   ........... C07D 237/24

OTHER PUBLICATIONS

Zhang et al. Nature Chem. 2015, 120-128. (Year: 2015).*
Briard et al. J. Label Compd Radiopharm. 2004, 217-232. (Year: 2004).*
Blom et al. J. Label. Compd Radiopharm. 2009, 52, 504-511.*
Pun et al. J. Nucl. Med. 2010, 51 (supp 2) 534. (Year: 2010).*
Elisabeth Blom et al: [ 18 F]/ 19 F exchange in fluorine containing compounds for potential use in 18 F-labelling strategies 11 , Journal of Labelled Compounds and Radiopharmaceuticals, vol. 52, No. 12, Aug. 25, 2009 (Aug. 25, 2009), pp. 504-511.
Jacobson et al., Novel Method for Radiolabeling and Dimerizing Thiolated Peptides Using 18F-Hexafluorobenzene, Bioconjugate Chem. 2015, 26, 2016-2020.
PUBCHEM CID 67949. pp. 1-21. Create Date: Mar. 26, 2005; p. 3. see 2D Structure.
International Search Report Issued for PCT Application No. PCT/US2018/022160 dated Jul. 26, 2018.

* cited by examiner

*Primary Examiner* — Michael G. Hartley
*Assistant Examiner* — Sean R Donohue
(74) *Attorney, Agent, or Firm* — Nguyen Tarbet LLC

(57) ABSTRACT

A method for preparing $^{18}$F radiolabeled biomolecules and agents for $^{18}$F-PET imaging is disclosed herein. A perfluoroaryl-conjugated target tracer is synthesized and purified with temperature and solvent conditions that are mild for the tracer molecule. The purified perfluoroaryl-conjugated target tracer is then labeled with $^{18}$F using $^{18}$F salts within a short reaction time, and with temperature and solvent conditions that are mild for the tracer molecule. The method provides a quick and convenient process that maintains the biological activities of the target molecules. The radiolabeled biomolecules may be used as contrast agents for Positron Emission Tomography (PET).

15 Claims, 2 Drawing Sheets

METHOD OF SYNTHESIZING $^{18}$F RADIOLABELED BIOMOLECULAR AGENTS

CROSS REFERENCE

This application claims priority to U.S. Patent Application No. 62/470,735, filed Mar. 13, 2017, the specification(s) of which is/are incorporated herein in their entirety by reference.

FIELD OF THE INVENTION

The present invention relates to chemical synthesis methods that can conveniently and rapidly label biomolecules and other small molecules with 18-fluorine ($^{18}$F), a radioactive version of the fluorine atom. These radiolabeled biomolecules can then be used as contrast agents for Positron Emission Tomography (PET).

BACKGROUND OF THE INVENTION

Positron emission tomography (PET) is a type of nuclear medicine imaging that utilizes small amounts of radioactive material, called radiopharmaceuticals or radiotracers, to diagnose and evaluate medical conditions, including cancers, heart disease, neurological disorders, and other abnormalities within the body. In particular, the PET procedure can evaluate the metabolism of a specific organ or area of the body, and provide information about its physiology, anatomy, and biochemical properties. The radiotracer may be injected, swallowed or inhaled into the body, and it accumulates in the organ or area of the body being examined. As the radiotracer decays, an imaging device detects its radioactive emissions, namely, positron emissions, and produces an image map from which said information can be evaluated.

Conventional radiotracers may comprise a molecule radiolabeled with a radioactive atom, such as $^{15}$O, $^{18}$F, $^{11}$C, or $^{13}$N. Of said radioactive atoms, fluorine-18 ($^{18}$F) is most preferred due to its longer half life (<120 min), as compared to the half lives of the other atoms; for instance, 11C has a half life of about 20 minutes. The longer half life of $^{18}$F allows for chemical reactions with $^{18}$F and other compounds to produce the radiotracer, and further allows for longer PET examinations. There is a growing interest in the radiolabeling of biomolecules, such as antibodies, minibodies, scFv, mRNA, siRNA, DNA, carbohydrates, peptides, glycoproteins, and the like, with a radionuclide, such as $^{18}$F, in order to produce a highly-specific targeting PET tracer. The biomolecule is preferably a chemical substance that is part of the natural metabolic process of the target organ or tissue. For example, a radioactive atom may be applied to glucose to produce a radiotracer for a PET scan of the brain. However, this technology is limited by costs, the half-life of the $^{18}$F radioisotope, and reaction conditions in preparing said $^{18}$F radioisotope and then attaching it to the biomolecule, One method of producing $^{18}$F requires the use of an expensive cyclotron, The $^{18}$F ion must then be chemically incorporated into a molecule, purified, and administered to the subject. In addition, since the radiotracer will require some time to accumulate at the target organ or area, this process must be performed rapidly and efficiently such that there is a sufficient amount of the $^{18}$F radioisotope still active for producing a quality image of the target organ or area. Alternatively, $^{18}$F salts, such as sodium fluoride or potassium fluoride, may be used to prepare the radiotracer. However, due to the relatively harsh reaction conditions, such as high temperatures and harsh solvents, to incorporate the $^{18}$F ion, direct radiofluorination is usually incompatible with the biomolecule, and would further require an intermediate compound for radiolabeling the biomolecule, Again, this method must be done in a relatively short time frame to ensure that there is sufficient radioactivity in the $^{18}$F radioisotope for imaging purposes. Therefore, there is a need for a facile process to radiolabel biomolecules with $^{18}$F while maintaining radioactivity.

An example of a conventional method is disclosed in Jacobson et al, ("Novel Method for Radiolabeling and Dimerizing Thiolated Peptides Using $^{18}$F-Hexafluorovenzene", DOI: 10,1021/acs.bioconjchem,5b00278. *Bioconjugate Chem.* 2015, 26, 2016-2020). Jacobson et al. teaches a first approach in which a perfluoroaryl molecule was conjugated to a biomolecule. Then the $^{18}$F/$^{19}$F exchange step was performed at a required a reaction temperature of 90° C. to make an intermediate hot (i.e. radioactive) PET molecule from the intermediate cold (i.e. not radioactive) compound, where the reaction time was 15 min and the yield was 33%, In the end, Jacobson et al. deemed the conditions for the $^{18}$F/$^{19}$F exchange step to be too harsh for the biomolecule attached to the perfluoroaryl molecule. Jacobson et al. further teaches a second approach in which the order of these two steps was switched. First the $^{18}$F/$^{19}$F exchange step was performed on a PFA compound using harsh conditions. Then, the hot PFA compound was conjugated to a biomolecule, which needed 20-25 min for 50% conjugation and then additional time for purification, Both of these procedures require a skilled chemist or radiochemist because they are advanced forms of synthesis.

The present invention features a chemical synthesis method that conveniently and rapidly labels biomolecules and other small target molecules with $^{18}$F. This method uses radioactive $^{18}$F that is readily available and does not require sophisticated radiochemistry, thereby eliminating the need for an expensive cyclotron or advanced radiochemistry expertise on-site.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a methodology for the design and synthesis of MRI/'$^{8}$F-PET and/or $^{18}$F labeling of biomolecules for $^{18}$F-PET imaging. According to one embodiment, the method may comprise synthesizing and purifying a perfluoroaryl-conjugated target tracer, where the tracer includes a molecule, such as a biomolecule, that can only undergo reactions under mild conditions. The purified perfluoroaryl-conjugated target tracer is then labeled with $^{8}$F using $^{18}$F salts within a short reaction time. Excess $^{18}$F salts can be removed using a simple dialysis or chromatography using SEP-PAK columns. Preferably, the conjugation reactions may be performed by a skilled chemist, whereas the $^{18}$F radiolabeling may be done experts and even non-experts at the location of the PET imaging instrument.

One of the unique and inventive technical features of the present invention is the method involves relatively mild reaction conditions that are tolerable by biomolecules. In particular, the perfluoroaryl moiety that is attached to the biomolecule or other target tracer undergoes a $^{19}$F-to-$^{18}$F substitution under mild temperatures and solvent conditions that do not harm the biological moiety. Without wishing to limit the invention to any theory or mechanism, it is believed that the technical feature of the present invention advantageously provides for a quick procedure to radiolabel the biomolecules while retaining their biological activities. None of the presently known prior references or work has the unique inventive technical feature of the present invention.

Another unique and inventive technical feature of the present invention is the use of water-soluble perfluoroaryl compounds. Alternatively, the present invention features methods of modifying perfluoroaryl compounds to increase their water-solubility. Without wishing to limit the invention to any theory or mechanism, it is believed that the technical feature of the present invention advantageously allows for relatively mild reaction conditions that maintains the biological activities of the biomolecules. Again, none of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1:
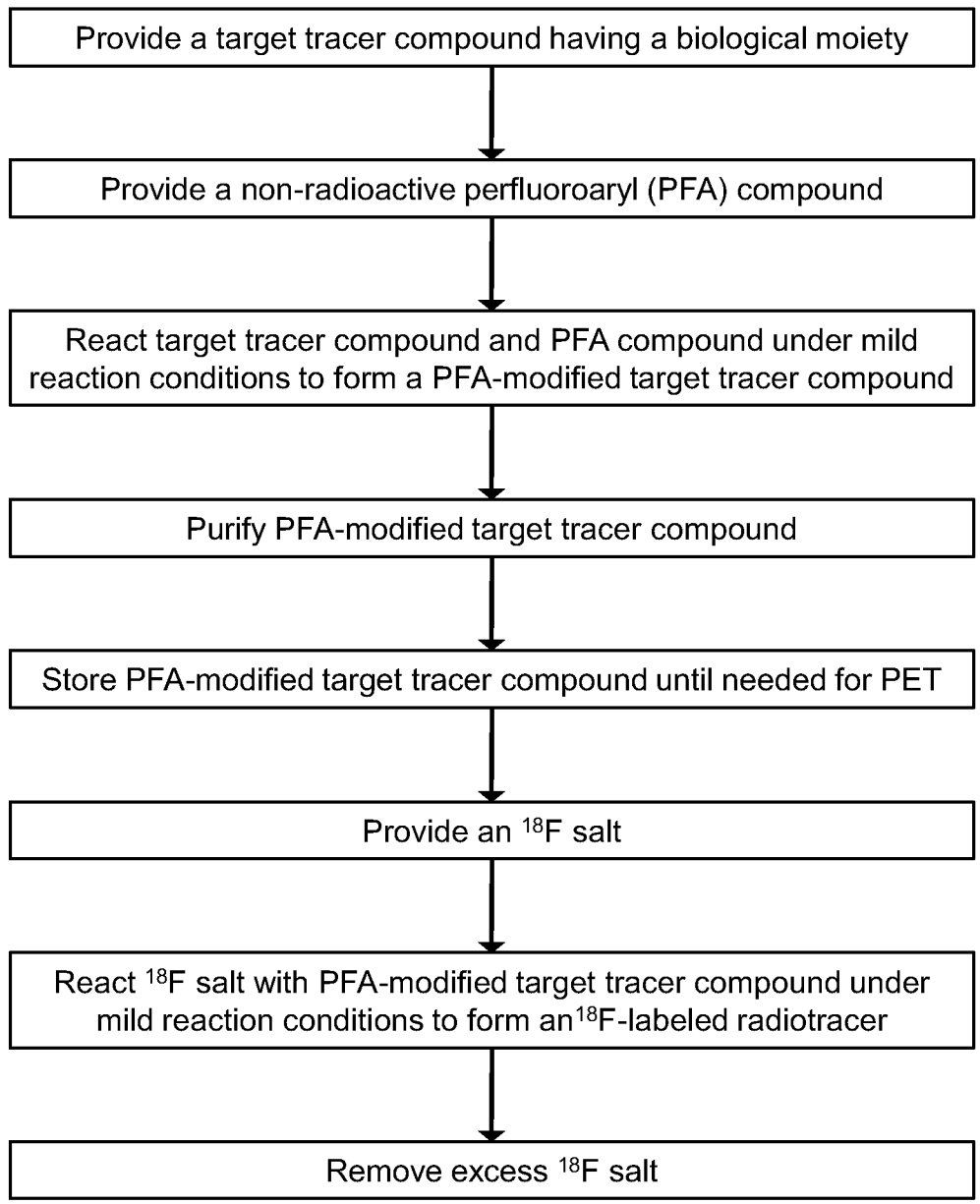
FIG. 1 shows a non-limiting methodology flow chart of the present invention.

As used herein, a "target tracer compound", or alternatively, "a target tracer molecule", or simply, a "target tracer", refers to a species that includes a moiety, such as a biomolecule, that can only be used in reactions under mild conditions, and is radiolabeled for use as a radiotracer (i.e. radiolabeled target tracer) in an imaging procedure, such as PET. Examples of said target tracers include, but are not limited to, any MRI, ultrasound, X-Ray, CT, or fluorescent agents that would also be detectable by PET; phospholipids, polyethylene glycols (PEG), PEGylated phospholipids; and biomolecules including peptides, mRNA, siRNA, snRNA, scFv, DNA, carbohydrates, cofactors, coenzymes, hormones, antibodies, minibodies, glycoproteins, and the like. The target tracer is distinct from and should not be confused nor interchanged with an intermediate compound, which refers to a prosthetic or carrier molecule that may be used to incorporate the radioactive atom into the target tracer, but has no direct use as a radiotracer in the imaging procedure.

As used herein, the term "mild" refers to reaction conditions in which the biological activity of the moiety in the target tracer compound is maintained and unaffected by said conditions. For example, mild reaction conditions can prevent denaturation of a protein molecule, thereby maintaining its native confirmation. In some embodiments, a mild temperature refers to a temperature in the range of about 15-37° C. or ambient temperature. In other embodiments, a mild reaction condition can be achieved by refraining from use of radiation, heat, and harsh compounds such strong acids, strong bases, concentrated inorganic salts, volatile solvents.

As used herein, a perfluoroaryl (PFA) compound refers to a fluorinated molecule comprising a plurality of fluorine atoms attached to an aromatic ring or aromatic ring system. The number of fluorine atoms may range from 4-6 per ring. In some embodiments, a variety of PFA compounds may be used in accordance with the present invention. Examples of the PFA compounds include, but are not limited to, the compounds shown in FIG. 2. In some embodiments, 'n' can range from 2-8.

In some embodiments, the present invention aims to provide methods of synthesizing of MRI/$^{18}$F-PET and/or $^{18}$F labeling of biomolecules for $^{18}$F-PET imaging. The methods that will be described herein feature reactions under mild conditions that are tolerable by biomolecules, such as antibodies, minibodies, scFv, mRNA, siRNA, DNA, carbohydrates, and glycoproteins.

In other embodiments, the solubility and reaction rate of the PFAs can vary for each compound. Without wishing to limit the invention to a particular theory or mechanism, the PFA compounds may be modified to alter their solubility and reaction rate. For example, a PFA compound having a poor solubility may be connected to water-soluble linkers, such as amino or thiol PEG, thereby increasing its solubility in aqueous solutions. Hence, it is another objective of the present invention to provide for water soluble PFA compounds for use in the methods described herein.

According to some embodiments, the present invention features a method of preparing $^{18}$F-labeled radiotracer for use in positron emission tomography (PET), The method may comprise providing a target tracer compound having a biological moiety, providing a non-radioactive perfluoroaryl (PFA) compound, reacting the target tracer compound and the PFA compound, thereby forming a non-radioactive PFA-modified target tracer compound, providing an $^{18}$F salt, and reacting the $^{18}$F salt with the PFA-modified target tracer compound, thereby forming the $^{18}$F-labeled radiotracer. In some embodiments, the method may further comprise purifying the PFA-modified target tracer compound subsequently after the reaction. In some other embodiments, the method may further comprise removing excess $^{18}$F salt from the second aqueous solvent after the $^{18}$F-labeled radiotracer is formed. For example, the excess $^{18}$F salt can be removed using dialysis or chromatography. Without wishing to limit the invention to a particular theory or mechanism, the method may be effective for preserving a biological activity of the biological moiety.

In some embodiments, the target tracer compound may be any molecule that has a biological moiety. In other embodiments, the target tracer compound may be a biomolecule, Non-limiting examples of the target tracer compound include any magnetic resonance imaging (MRI) agents, ultrasound agents, x-ray agents, computerized tomography (CT) agents, or fluorescent agents that are detectable by PET, phospholipids, polyethylene glycols (PEG), PEGylated phospholipids, peptides, mRNA, siRNA, snRNA, scFv, DNA, and fragments thereof, carbohydrates, cofactors, coenzymes, hormones, antibodies, minibodies, and glycoproteins.

According to other embodiments, the target tracer compound may further comprise a functional group that reacts with the PFA compound via aromatic nucleophilic substitution (SNAr). In one embodiment, the functional group may be

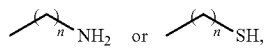

where n ranges from 0-5.

In some embodiments, the step of providing the PFA compound may comprise modifying a base PFA compound with a water-soluble functional group, thereby increasing a solubility of the PFA compound to produce a water-soluble PFA compound. In some embodiments, the water-soluble functional group is an amino, a thiol, or a thiol PEG group. In one embodiment, the PFA compound can be any of the PFA compounds disclosed herein, for example, such as those shown in FIG. 2 with n ranging from 2-8.

In preferred embodiments, the target tracer compound and the PFA compound are reacted in a first aqueous solvent at a first ambient temperature that is mild for the biological moiety such that the biological activity of the biological moiety is preserved. In one embodiment, the first aqueous solvent is predominantly water. In another embodiment, the first aqueous solvent may further comprise a base. The base of the first aqueous solvent may be effective for increasing the nucleophilicity of the target tracer compound. Examples of said base include, but are not limited to, tris(hydroxymethyl)aminomethane, phosphate, diisopropylethylamine, and 4-(2-hydroxyethyl)piperazine-1-ethanesulfonic acid. In some embodiments, the base is present at a range of about 1%-5% vol, or about 5%-10% vol, or about 10%-15% vol, or about 15-20% vol, including any ranges in between said values.

In another embodiment, the first aqueous solvent may further comprise about 1%-10% vol of a co-solvent. Non-limiting examples of the co-solvent include dimethyl sulfoxide, dimethylformamide, or acetonitrile. Preferably, the co-solvent may be effective for increasing a solubility of the target tracer compound. In some embodiments, the co-solvent is present at a range of about 1%-4% vol, or about 4%-7% vol, or about 7%-10% vol, including any ranges in between said values. In a preferred embodiment, the amount of the co-solvent is up to about 5% vol.

In some embodiments, the first ambient temperature can range from about 15° C. to about 37° C., including any ranges in between said values. For example, the first ambient temperature is about 15-20° C., or about 20-25° C., or about 25-30° C., or about 30-37° C., including any ranges in between said values. In other embodiments, the first ambient temperature is at most about 37° C.

In some embodiments, prior to reacting the PFA-modified target tracer with the $^{18}$F salt, the PFA-modified target tracer compound can be stored for a period of time until an $^{18}$F-labeled radiotracer is required for use in PET. For instance, the PFA-modified target tracer compound may be stored for a period of time ranging from days to months. When the $^{18}$F-labeled radiotracer is required for PET, the stored PFA-modified target tracer compound is reacted with the $^{18}$F salt to form the $^{18}$F-labeled radiotracer.

In other preferred embodiments, the $^{18}$F salt is reacted with the PFA-modified target tracer compound in a second aqueous solvent at a second ambient temperature that is mild for the biological moiety such that the biological activity of the biological moiety is preserved. Non-limiting examples of the $^{18}$F salt include Na$^{18}$F, K$^{18}$F, or K$^{18}$FK$_{2.2.2}$. Without wishing to limit the invention to a particular theory or mechanism, the $^{18}$F-labeled radiotracer is formed when an $^{18}$F radioisotope of the $^{18}$F salt replaces any of the $^{19}$F isotopes in the PFA-modified target tracer compound. Preferably, the $^{18}$F-labeled radiotracer if formed in about 10 to 20 minutes; for example, in about 15 minutes.

In some embodiments, the second aqueous solvent may be predominantly water. In other embodiments, the second aqueous solvent may further comprise about 1%-10% vol of a co-solvent that is effective for increasing a solubility of the PFA-modified target tracer compound. Examples of the co-solvent include, but are not limited to, dimethyl sulfoxide, dimethylformamide, or acetonitrile. In still other embodiments, the co-solvent is present at a range of about 1%-4% vol, or about 4%-7% vol, or about 7%-10% vol, including any ranges in between said values. In a preferred embodiment, the amount of the co-solvent is up to about 5% vol.

In one embodiment, the second ambient temperature can range from about 15° C. to about 37° C., including any ranges in between said values. For example, the second ambient temperature is about 15-20° C., or about 20-25° C., or about 25-30° C., or about 30-37° C., including any ranges in between said values. In another embodiment, the second ambient temperature is at most about 37° C.

According to some embodiments, the present invention features a kit for preparing an $^{18}$F-labeled radiotracer for use in positron emission tomography (PET). In one embodiment, the kit may comprise a perfluoroaryl (PFA)-modified target tracer compound, an $^{18}$F salt, and a set of instructions for preparing the $^{18}$F-labeled radiotracer prior to use in PET such that the biological activity of the biological moiety is preserved. In some embodiments, the perfluoroaryl (PFA)-modified target tracer compound may comprise a PFA compound covalently bound to a target tracer compound having a biological moiety in which its biological activity is preserved. Preferably, the PFA-modified target tracer compound is non-radioactive. In another embodiment, the PFA-modified target tracer compound may be a purified form.

In some embodiments, the set of instructions may comprise an instruction for reacting the 18F salt with the PFA-modified target tracer compound in an aqueous solvent at an ambient temperature that is mild for the biological moiety such that its biological activity is preserved. During the reaction, an $^{18}$F radioisotope of the $^{18}$F salt is configured to replace an $^{19}$F isotope of the PFA-modified target tracer compound, thereby forming the $^{18}$F-labeled radiotracer. In other embodiments, the set of instructions may further comprise an instruction for removing excess 18F salt after the 18F-labeled radiotracer is formed.

Figure 2:
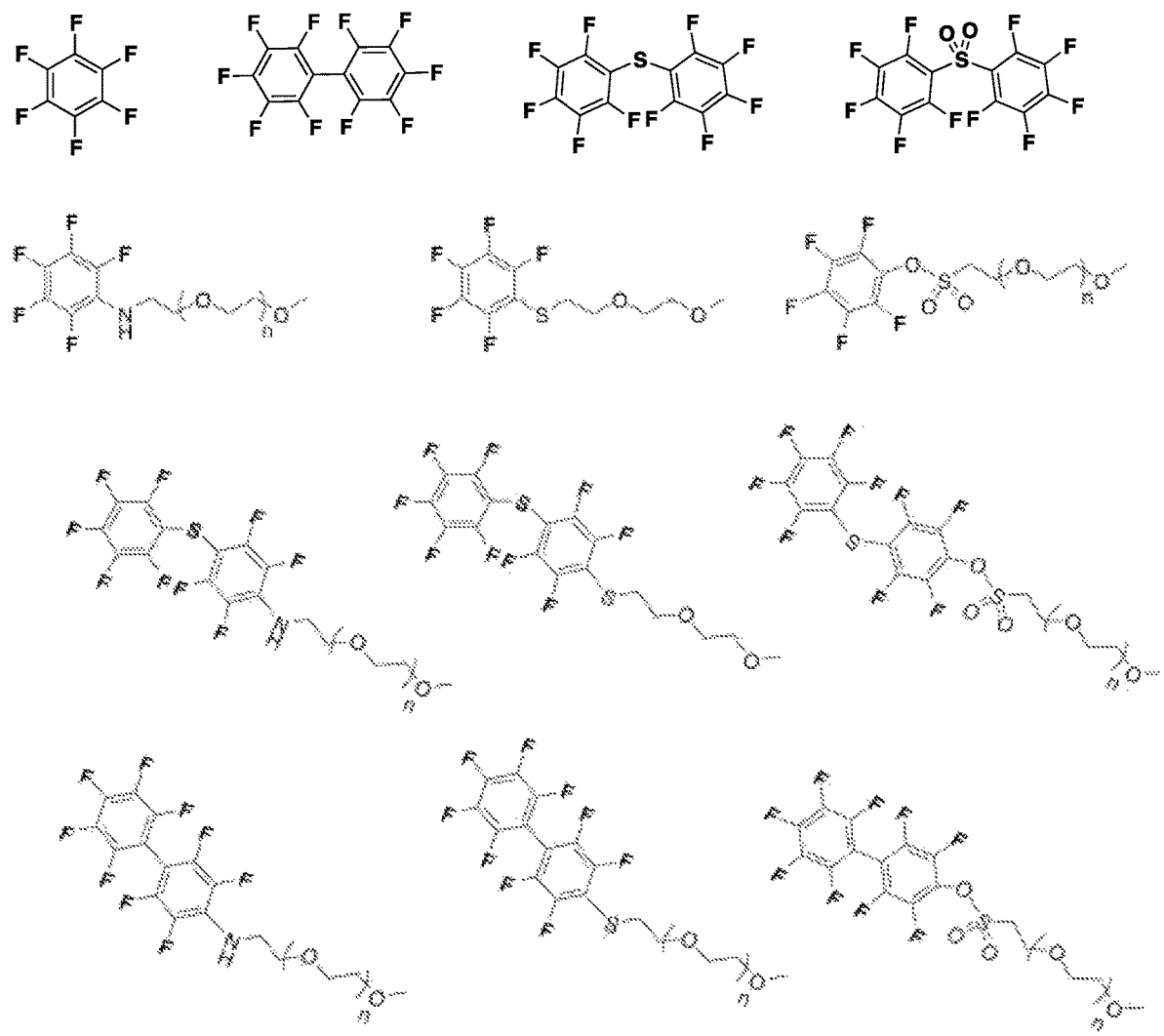
FIG. 2 shows non-limiting examples of perfluoroaryl (PFA) compounds that may be used in accordance with the present invention.

In some embodiments, the target tracer compound includes magnetic resonance imaging (MRI) agents, ultrasound agents, x-ray agents, computerized tomography (CT) agents, and fluorescent agents that are detectable by PET, phospholipids, polyethylene glycols (PEG), PEGylated phospholipids, peptides, mRNA, siRNA, snRNA, scFv, DNA, and fragments thereof, carbohydrates, cofactors, coenzymes, hormones, antibodies, minibodies, or glycoproteins. In other embodiments, the PFA compound may be compounds as shown in FIG. 2. In still other embodiments, the $^{18}$F salt may be Na$^{18}$F, K$^{18}$F, or K$^{18}$FK$_{2.2.2}$.

EXAMPLES

The following are non-limiting examples of preparing an $^{18}$F-radiolabeled biomolecule in accordance with the present invention. The examples are for illustrative purposes only and are not intended to limit the invention in any way. Equivalents or substitutes are within the scope of the invention.

Step 1: An MRI agent or a biomolecule is conjugated to PFA in an aqueous solution under mild conditions, as shown in Scheme 1.

Scheme 1. Conjugation of PFA to the biomolecule of interest.

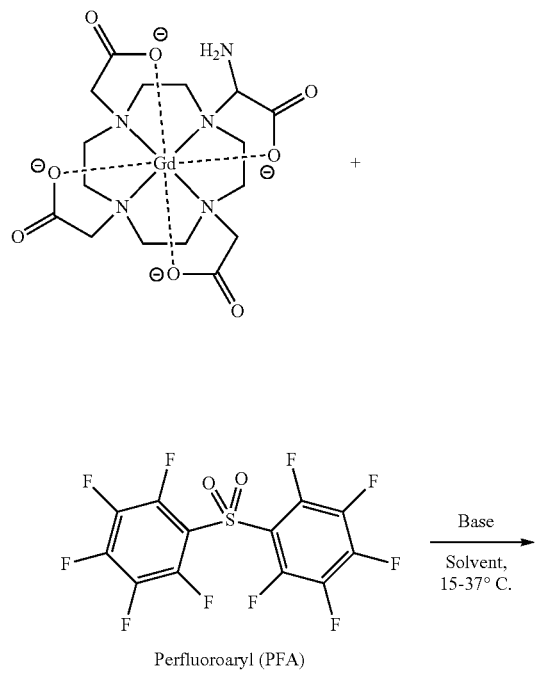

Perfluoroaryl (PFA)

Scheme 2. $^{18}$F/$^{19}$F exchange step.

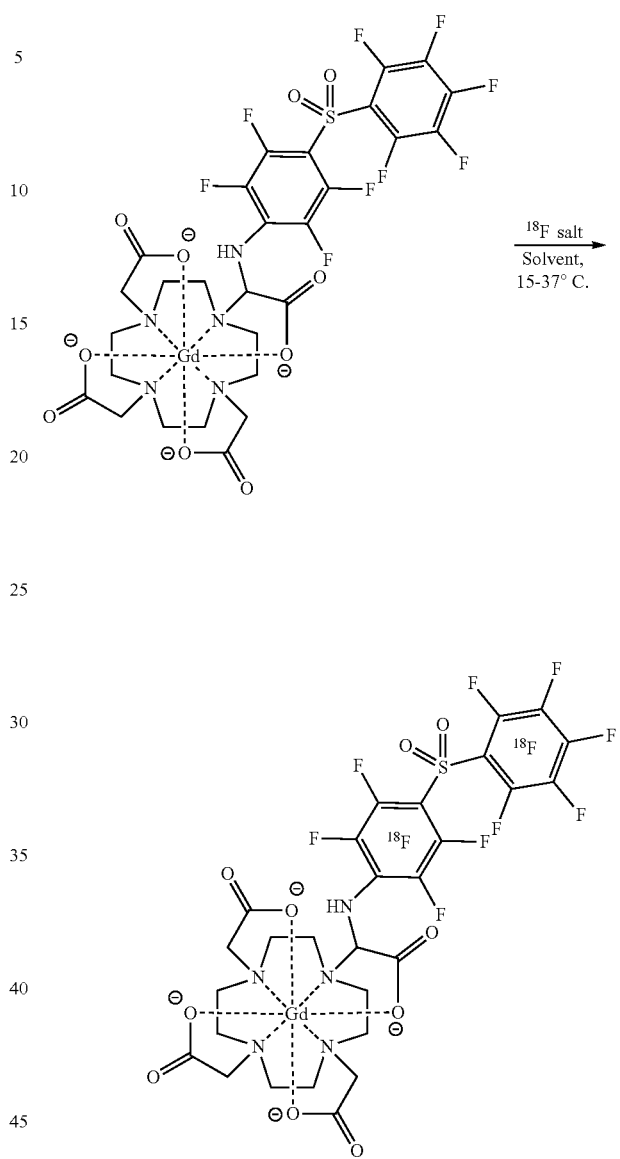

In some embodiments, water may be the main solvent for this reaction. However, other co-solvents, such as DMSO, DMF, and ACN (up to 5%), may be added to the water if the MRI agent, biomolecule, or PFA has poor solubility in water. In other embodiments, the base may be TRIS, phosphate, DIPEA, or HEPES. Preferably, the base may be effective to increase the nucleophilicity of the MRI agent or biomolecule. In preferred embodiments, the reaction may be performed at a mild temperature range for the biomolecule. For example, the temperature can range from about 15-37° C.

Step 2: $^{18}$F salts are added to the solution of PFA-conjugated MRI agent or biomolecule, as shown in Scheme 2. $^{18}$F/$^{19}$F exchange can occur rapidly in this step.

In some embodiments, water may be the main solvent for the reaction. However, other co-solvents, such as DMSO, DMF, and ACN (up to 5%), may be added to the water if the MRI agent, biomolecule, or PFA has poor solubility in water. In other embodiments, the $^{18}$F salt may be Na$^{18}$F, K$^{18}$FK$_{2.2.2}$, or similar compounds. This reaction is also performed at a mild temperature range for the biomolecule. In one embodiment, the temperature can range from about 15-37° C. Without wishing to limit the invention to a particular theory or mechanism, the present methodology advantageously utilizes reaction conditions that are harmless for biomolecules, thereby retaining their biological activity.

Scheme 3 shows another non-limiting example of the reaction procedure. The MRI agent or a biomolecule is conjugated to PFA in an aqueous solution under mild conditions, and then $^{18}$F salts are added to the solution of the PFA-conjugated MRI agent or biomolecule, thereby producing the $^{18}$F radiolabeled MRI agent or biomolecule.

Scheme 3. Synthesis of $^{18}$F radiolabeled PET tracer.

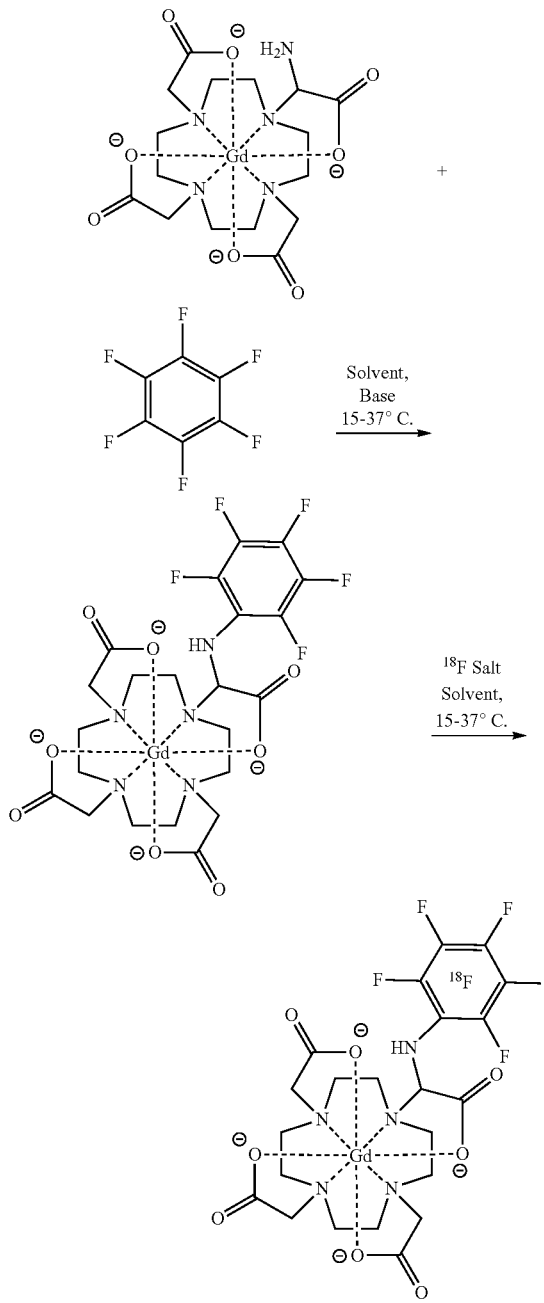

As shown in the previous examples, the biomolecule or MRI agent can be conjugated to a cold (i.e. non-radioactive) PFA compound and the product may be purified. Since the PFA-modified target tracer lacks any radioactivity, the reaction and purification steps can proceed without any urgency or time limitations. In some embodiments, the PFA-modified target tracer is stable for a period of time (ca. days to months). Hence, the step of $^{18}$F/$^{19}$F exchange may be performed at a later time and at a different location from when and where the PFA-modified target tracer is prepared. Further still, a non-chemist or one having only ordinary skill can perform this step of mixing the PFA-modified target tracer with an $^{18}$F salt to produce the PET radiotracer, which may have a reaction time as short as 10 minutes. In other embodiments, the PET radiotracer may be ready for use after a simple dialysis step to remove excess $^{18}$F salts. Systems and methods of dialysis are known to one of ordinary skill in the art.

According to some embodiments, conjugation reactions may be followed by a purification step to isolate the conjugated product from any unconjugated compounds. Without wishing to limit the invention to a particular theory or mechanism, given that the purification of $^{18}$F-labeled materials requires some special conditions and/or equipment, the present invention conveniently performs all chemical reactions and purifications prior to the $^{18}$F/$^{19}$F exchange step. In addition, since the radioactive $^{18}$F atom has a half-life of about 109 minutes, it is more beneficial and efficient to perform the $^{18}$F/$^{19}$F exchange as the final step, or just prior to the desired time of administering the radiotracer to the subject. Contrary to the present invention, the radioactivity of $^{18}$F decreases to a much greater extent during the longer synthesis and purification steps disclosed in the procedure of Jacobson et al.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of preparing an $^{18}$F-labeled radiotracer for use in positron emission tomography (PET), said method comprising:
    a. providing a target tracer compound having a biological moiety;
    b. providing a non-radioactive, water-soluble perfluoroaryl (PFA) compound;
    c. reacting the target tracer compound and the water-soluble PFA compound in a first aqueous solvent that is predominantly water, at a first ambient temperature that is mild for the biological moiety, thereby forming a PFA-modified target tracer compound, wherein the PFA-modified target tracer compound is non-radioactive, and wherein a biological activity of the biological moiety is preserved;
    d. providing an $^{18}$F salt; and
    e. reacting the $^{18}$F salt with the PFA-modified target tracer compound in a second aqueous solvent that is predominantly water, at a second ambient temperature that is mild for the biological moiety, wherein an $^{18}$F radioisotope of the $^{18}$F salt replaces an $^{19}$F isotope of the PFA-modified target tracer compound, thereby forming the $^{18}$F-labeled wherein the first ambient temperature and the second ambient temperature is at most about 37° C., wherein the biological activity of the biological moiety is preserved.

2. The method of claim 1, wherein reacting the $^{18}$F salt with the PFA-modified target tracer forms the $^{18}$F-labeled radiotracer in about 10 to 20 minutes.

3. The method of claim 1, wherein the target tracer compound is selected from a group consisting of magnetic resonance imaging (MRI) agents, ultrasound agents, x-ray agents, computerized tomography (CT) agents, and fluorescent agents that are detectable by PET, phospholipids, polyethylene glycols (PEG), PEGylated phospholipids, peptides, mRNA, siRNA, snRNA, scFv, DNA, and fragments thereof, carbohydrates, cofactors, coenzymes, hormones, antibodies, minibodies, and glycoproteins.

4. The method of claim 1, wherein the target tracer compound comprises a functional group that reacts with the PFA compound via aromatic nucleophilic substitution (SNAr).

5. The method of claim 4, wherein the functional group is

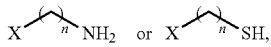

wherein n ranges from 0-5.

6. The method of claim 1, wherein providing the water-soluble PFA compound comprises modifying a base PFA compound with a water-soluble functional group to increase a solubility of the PFA compound, thereby to producing the water-soluble PFA compound.

7. The method of claim 6, wherein the water-soluble functional group is an amino, a thiol, or a thiol PEG group.

8. The method of claim 1, wherein the PFA compound is selected from a group consisting of the following:

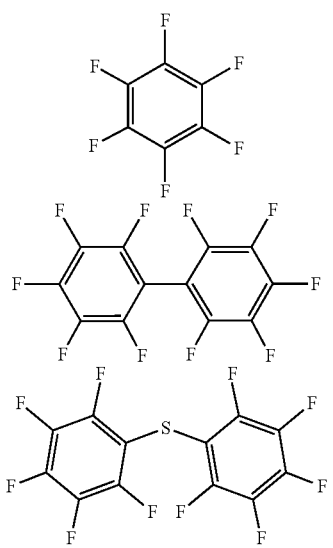

-continued

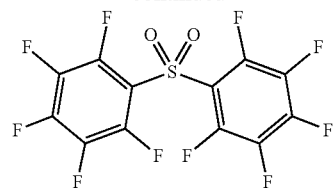

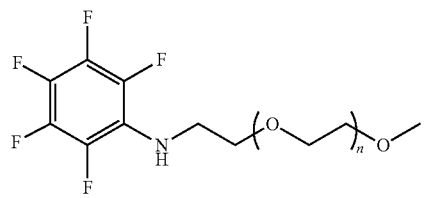

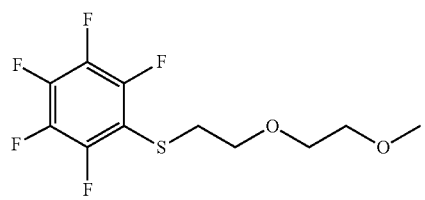

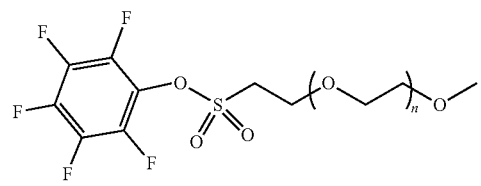

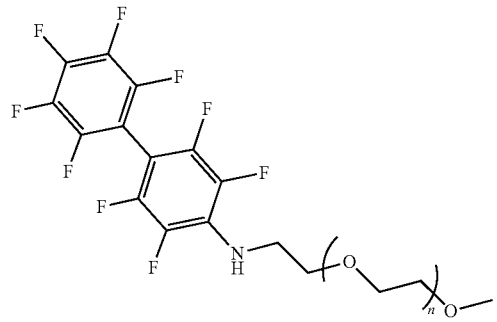

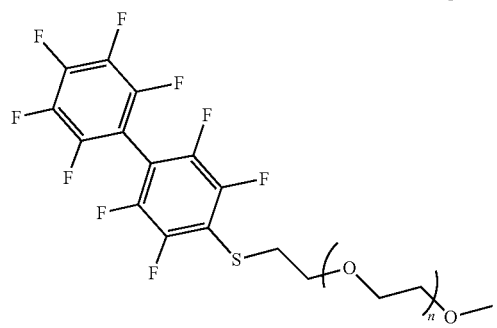

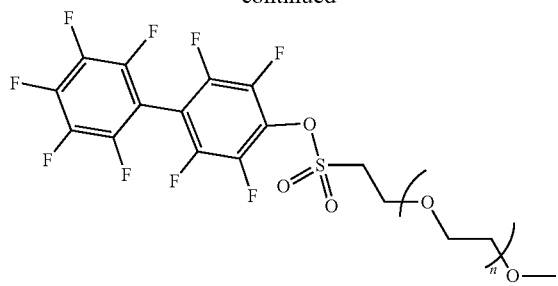

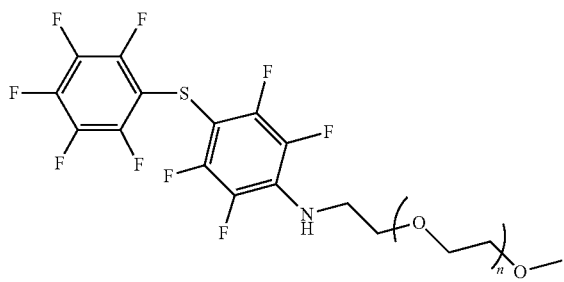

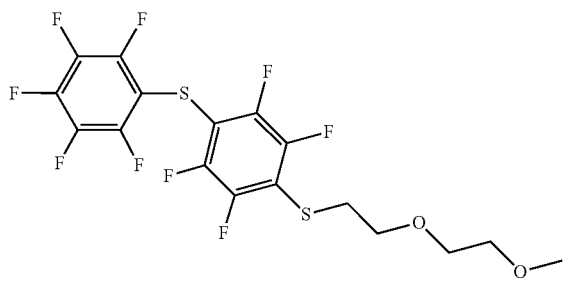

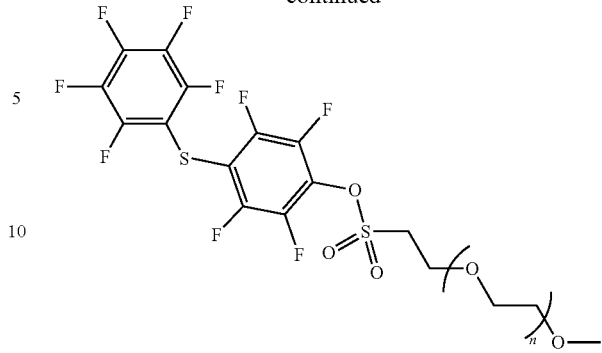

wherein n ranges from 2-8.

9. The method of claim 1, the first aqueous solvent further comprises a base effective for increasing a nucleophilicity of the target tracer compound.

10. The method of claim 9, wherein the base of the first aqueous solvent is tris(hydroxymethyl)aminomethane, phosphate, diisopropylethylamine, or 4-(2-hydroxyethyl)piperazine-1-ethanesulfonic acid.

11. The method of claim 1, wherein the first aqueous solvent further comprises about 1%-10% vol of a co-solvent, wherein the co-solvent is effective for increasing a solubility of the target tracer compound.

12. The method of claim 11, wherein the co-solvent is dimethyl sulfoxide, dimethylformamide, or acetonitrile.

13. The method of claim 1, wherein the second aqueous solvent further comprises about 1%-10% vol of a co-solvent, wherein the co-solvent is effective for increasing a solubility of the PFA-modified target tracer compound.

14. The method of claim 13, wherein the co-solvent is dimethyl sulfoxide, dimethylformamide, or acetonitrile.

15. The method of claim 1, wherein the $^{18}F$ salt is $Na^{18}F$, $K^{18}F$, or $K^{18}KF_{2.2.2.}$.

* * * * *